United States Patent
Clok et al.

(10) Patent No.: US 6,685,683 B1
(45) Date of Patent: Feb. 3, 2004

(54) OSTOMY APPLIANCE SHOWING ADHESIVE, BARRIER AND ABSORBING PROPERTIES

(75) Inventors: Danuta Clok, Nivaa (DK); Per Ole Nielsen, Broenshoel (DK); Inger Mann Nielsen, Frederlksberg (DK)

(73) Assignee: Coloplast A/S, Humlebaek (DK)

(*) Notice: Subject to any disclaimer, the term of this patent is extended or adjusted under 35 U.S.C. 154(b) by 0 days.

(21) Appl. No.: 10/030,091

(22) PCT Filed: Jul. 13, 2000

(86) PCT No.: PCT/DK00/00395

§ 371 (c)(1),
(2), (4) Date: Jan. 15, 2002

(87) PCT Pub. No.: WO01/05340

PCT Pub. Date: Jan. 25, 2001

(30) Foreign Application Priority Data

Jul. 15, 1999 (DK) .................................. 1999 01033

(51) Int. Cl.$^7$ .................................................. A61F 5/44
(52) U.S. Cl. ..................................................... 604/344
(58) Field of Search .................. 604/327, 332–344, 604/355; 428/355 CP; 524/47

(56) References Cited

U.S. PATENT DOCUMENTS

| | | | | |
|---|---|---|---|---|
| 3,667,469 A | * | 6/1972 | Marsan ....................... 604/336 |
| 3,712,304 A | | 1/1973 | Marsan ....................... 128/283 |
| 3,713,445 A | | 1/1973 | Marsan ....................... 128/283 |
| 3,799,166 A | | 3/1974 | Marsan ....................... 128/283 |
| 3,908,658 A | | 9/1975 | Marsan ....................... 128/283 |
| 3,980,084 A | * | 9/1976 | Kross .......................... 604/336 |
| 4,231,369 A | * | 11/1980 | Sorensen et al. ............ 604/336 |
| 4,252,120 A | | 2/1981 | Carpenter ................... 128/283 |
| 4,253,460 A | | 3/1981 | Chen et al. ................. 128/283 |
| 4,393,080 A | | 7/1983 | Pawelchak et al. ......... 428/355 |
| 4,551,490 A | * | 11/1985 | Doyle et al. ................. 524/22 |
| 5,051,259 A | | 9/1991 | Olsen et al. ................. 424/443 |
| 5,629,079 A | * | 5/1997 | Battles et al. ................ 442/60 |
| 5,714,225 A | | 2/1998 | Hansen et al. .............. 428/114 |
| 5,730,736 A | | 3/1998 | Sawers et al. ............... 604/344 |
| 6,068,852 A | * | 5/2000 | Shah ............................ 424/443 |
| 6,451,883 B1 | * | 9/2002 | Chen et al. .................. 524/31 |

FOREIGN PATENT DOCUMENTS

| | | |
|---|---|---|
| EP | 0 130 061 | 1/1985 |
| EP | 0 272 149 | 6/1988 |
| EP | 0 388 924 | 9/1990 |
| EP | 0 586 267 | 3/1994 |
| GB | 1 586 182 | 3/1981 |
| WO | 89/05619 | 6/1989 |
| WO | 94/15562 | 7/1994 |
| WO | 99/11302 | 3/1999 |

* cited by examiner

*Primary Examiner*—Weilun Lo
*Assistant Examiner*—Michael G. Bogart
(74) *Attorney, Agent, or Firm*—Jacobson Holman PLLC

(57) ABSTRACT

In an ostomy appliance comprising an adhesive, flexible, skin barrier product for securing the appliance to the user's skin, said skin barrier having a hole for receiving a stoma, ureter or catheter, and said skin barrier comprising, in the surface to be secured to the user's skin, at least a first zone showing adhesive and barrier properties and a second zone showing moisture absorbing properties wherein the first zone comprises a substantially homogeneous mixture of from 15 to 95% by weight of one or more rubbery components and from 2 to 85% by weight of a starch, and furthermore may comprise from 0 to 60% by weight of one or more hydrocolloids, from 0 to 50% by weight of one or more tackifier resins, from 0 to 10% by weight of one or more plasticizers and from 0 to 5% by weight of a pigment, the barrier adhesive "behaves", in a dry state, Theologically as an adhesive comprising hydrocolloid but which does not absorb moisture in the presence of moisture. Thus, itching when the adhesive is placed on the skin and a light reddening after removal is avoided.

9 Claims, 1 Drawing Sheet

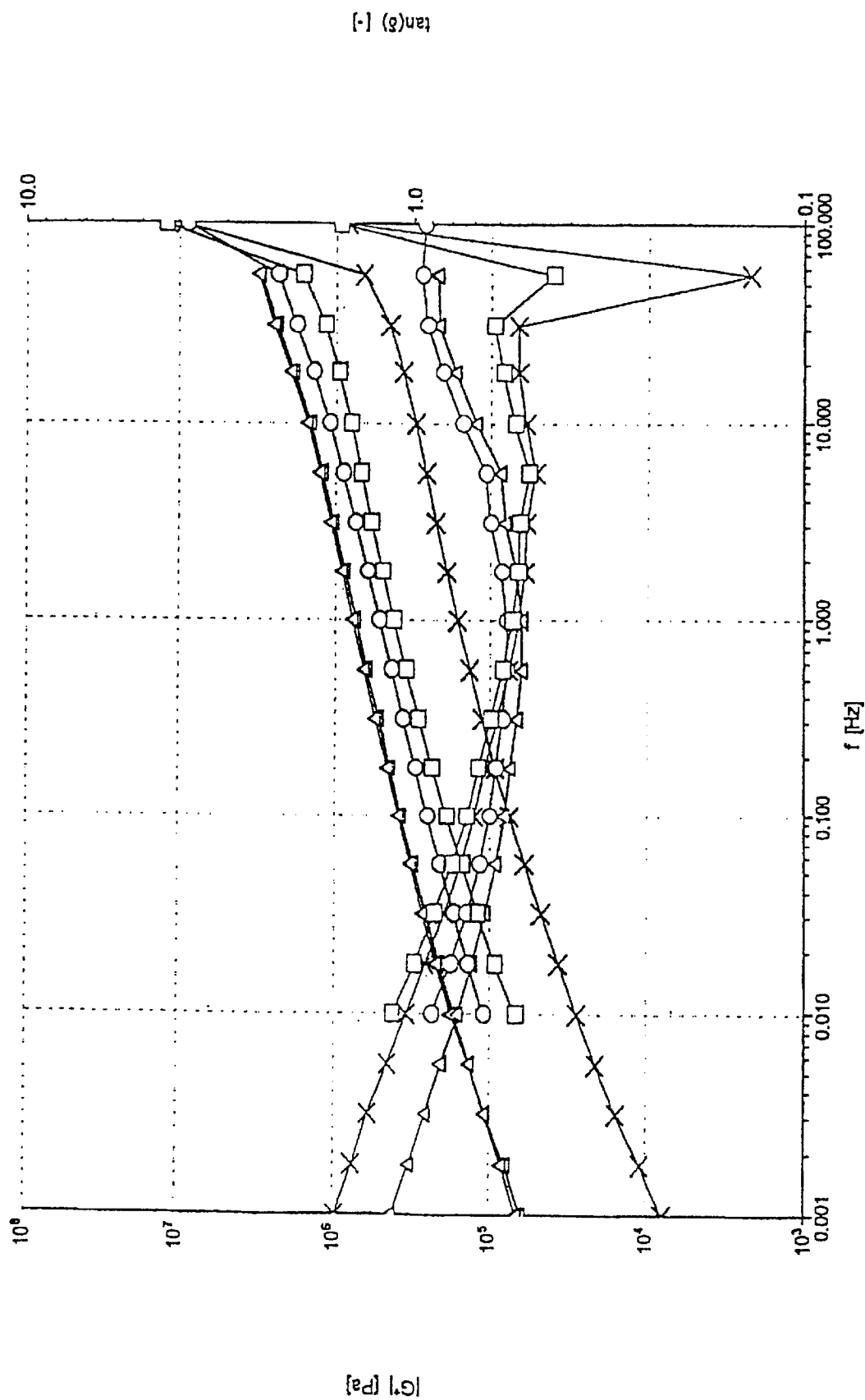

OSTOMY APPLIANCE SHOWING ADHESIVE, BARRIER AND ABSORBING PROPERTIES

This is a nationalization of PCT/DK00/00395 filed Jul. 13, 2000 and published in English.

BACKGROUND OF THE INVENTION

1. Field of the Invention

The present invention relates to an ostomy appliance comprising an adhesive, flexible skin barrier product for securing the appliance to the user's skin said barrier having a hole for receiving a stoma, ureter or catheter and barrier wafer showing improved capability of undergoing deformation owing to the user's movements, an adhesive flexible skin barrier product for use as a semi-manufacture in the production of dressings, skin and wound care devices, fastening means for wound care devices, fastening means for dressings, ostomy equipment, wound drains and incontinence equipment such as external catheters and for similar applications and for use in electrodes for application to the skin; and the use of a starch for modifying of the absorbing and rheological properties of the first zone of an adhesive, flexible, skin barrier product layer for an ostomy appliance comprising at least a first zone showing adhesive and barrier properties and a second zone showing moisture absorbing properties.

In connection with surgery for a number of diseases in the gastrointestinal or urinary tract a consequence is, in many cases, that the colon, the ileum or the ureter has been exposed surgically and the patient is left with an abdominal stoma, or, in nephrostomy or ureterostomy, the ureter or a catheter is exposed in the back or the chest region or abdominal region, and the effluents or waste products of the body, which are conveyed through these organs, are discharged through the artificial orifice or opening and are collected in a collection bag, which is usually adhered to the skin by means of an adhesive wafer or plate having an inlet opening for accommodating the stoma/ureter/catheter. Also in connection with a fistula, the patient will have to rely on an appliance to collect the bodily material emerging from such opening.

2. Description of the Related Art

Ostomy appliances are well known. Such appliances may be two-piece or one-piece appliances. In both types of appliances, an adhesive barrier member (or base plate) is attached to the wearer's abdomen/back/chest. In case of a one-piece appliance, a receiving member or bag is attached to the adhesive barrier. In case of a two-piece appliance, the adhesive barrier member forms part of a body side ostomy member and a receiving member or bag is attached releasably to the body side member for receiving exudates from the stoma.

When using one-piece appliances, the whole appliance, including the adhesive skin barrier securing the appliance to the skin is removed and replaced by a fresh appliance. When using two-piece appliances, the body side member is left in place up to several days, and only the receiving member or bag attached to the body side member is replaced. The attachment means for attaching an ostomy receiving bag may be a system known per se comprising matching coupling rings or matching flanges and adhesive surfaces engaging with and sealing against a flange area of the body side member.

For two-piece appliances, the service time of the body side member depends on the amount and aggressiveness of the exudates and of the tightness of the sealing between the stoma and the body side member.

In such a collecting system, the adhesive skin barrier of the body side member must be able to remain on the user over a long period of time, for example up to 8–10 days in order to minimise the irritation of the skin due to removal of the adhesive skin barrier, cleaning of the area and application of a fresh appliance. Users engaged in active employment prefer to have the option of exchanging the body side member only on a weekly basis for convenience.

WO 89/05619 and WO 94/15562 disclose skin barrier products comprising two or more essentially non-mixed materials having different properties. When using adhesive compositions designed to provide barrier properties, adhesiveness and grip for securing the skin barrier product to the skin, and adhesive compositions designed to provide moisture absorptive properties, respectively, the adhesive barrier part is often based on a material with very low or no absorbing properties which is often a relatively soft and tacky material whereas the moisture absorbing composition is relatively hard.

In the above system considerable differences in Theological properties will often be found between the moisture absorbing adhesives and the adhesives showing barrier properties. These differences in rheological properties are due to different formulations of the two adhesives, and especially the difference in content of hydrocolloids plays an important role. A comparison of a moisture absorbing adhesive and an adhesive having barrier properties wherein the proportions of polymer constituents, resins, plasticizers and oil are the same for both adhesives, but 40–60% hydrocolloids has been added to the moisture absorbing adhesive whereas the adhesive having barrier properties comprises no or only 5–10% hydrocolloids, shows that the moisture absorbing adhesive will appear harder (less elastic) than the adhesive having barrier properties.

In order to improve the service time and security against leakage the body side member must be capable of undergoing deformation owing to the user's movements, washing, exposure to bag replacements, etc. Conventionally, the base plate of such a carrier device is designed as a thin adhesive foil, optionally with some sort of stiffening reinforcement disc for maintaining a plane adhesive surface for the bag.

If the above types of adhesives are used in the systems disclosed in WO 89/05619 and WO 94/15562, the advantages disclosed therein will naturally be obtained with respect to spreading of absorbed water in the system. The spreading will naturally be minimised due to the barrier layer which, again, will lead to a minimising of the leaching. Considerable differences in rheological properties of the different zones of the base plate product may, however, give rise to processing problems and may cause skin problems on the user.

The process problems will be most pronounced when cutting the blank base plate products and during a later bevelling or contouring and punching of the product. A considerable difference in the hardness of the different zones may render the cutting process difficult as the structure of the products disclosed in WO 89/05619 and, hence, the desired properties, may be disturbed if the material is not kept sufficiently cold. During bevelling or contouring, the rheological differences between the different zones may cause the soft adhesive to be pressed over the harder adhesive at the surface to be in contact with the skin and this will of course disturb the design properties of the product and may cause problems for the patients.

Another problem which may be caused in a system disclosed in the patent applications referred to above due to the rheological differences is a mechanical stressing of the skin as the two adhesives function very differently. The soft barrier adhesive will easily be able to follow very small movements of the skin whereas this is not the case for the moisture absorbing adhesive. It may be compared to pinching the skin and may be experienced as itching when the adhesive is placed on the skin and a light reddening after removal.

Thus, when the patient moves or bends, the difference in rheological properties of the different materials may even give rise to lack of contact between the two materials. This may cause irritation due to opening and closure of small cracks in the surface of the skin barrier product which may cause direct physical irritation or reduce the time of service during which the skin barrier product is able to protect the skin against contact with the exudates from a stoma.

It is an object of the invention to eliminate these problems by rendering the different adhesives rheologically more alike.

Normally it is not possible to render the adhesive comprising hydrocolloids more soft without loosing the high absorption capacity.

The adhesive showing barrier properties must not be amended in a manner giving pronounced change of the barrier properties of the adhesive as this property is of great importance for the performance of the system. By addition of hydrocolloid it is possible to obtain the desired Theological properties but then, the adhesive will be absorbing when in contact with moisture leading to a loss of the barrier properties.

A change of the proportion between the polymer constituents, resins and plasticizer will cause a shift of the ratio between the viscous and elastic moduli of the adhesive which is undesirable.

It has now been found that it is possible to add a constituent with an inherently low water absorbing capacity which makes the barrier adhesive, in a dry state, "behave" Theologically as an adhesive comprising hydrocolloid but which does not swell in the presence of moisture. Furthermore, it has been found that it is possible to provide a barrier layer comprising hydrocolloids and showing low absorption and being Theologically similar to conventional moisture absorbing adhesives comprising hydrocolloids.

SUMMARY OF THE INVENTION

The present invention relates to an ostomy appliance comprising an adhesive, flexible skin barrier product for securing the appliance to the user's skin, said skin barrier having a hole for receiving a stoma, a ureter or a catheter and said skin barrier comprising, in the surface to be secured to the user's skin, at least a first zone showing adhesive and barrier properties and a second zone showing moisture absorbing properties.

Furthermore, the invention relates to an adhesive flexible skin barrier product for use as a semi-manufacture in the production of dressings, skin and wound care devices, fastening means for wound care devices, fastening means for dressings, ostomy equipment, wound drains and incontinence equipment such as external catheters and for similar applications and for use in electrodes for application to the skin.

Still further, the invention relates to the use of a starch in an amount of from 2 to 85% by weight for modifying of the Theological properties of a zone of an adhesive flexible, skin barrier product layer for an ostomy appliance comprising at least a first zone showing adhesive and barrier properties and a second zone showing moisture absorbing properties, said zone comprising a substantially homogeneous mixture of from 15 to 98% by weight of one or more rubbery components and furthermore may comprise from 0 to 60% by weight of one or more hydrocolloids, from 0 to 50% by weight of one or more tackifier resins, from 0 to 10% by weight of one or more plasticizers and from 0 to 5% by weight of a pigment.

BRIEF DESCRIPTION OF THE DRAWINGS

The present invention is explained more in detail with reference to the drawings showing a diagram of the rheological properties of an adhesive skin barrier product according to the invention.

DETAILED DESCRIPTION OF THE INVENTION

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

The present invention relates to an ostomy appliance comprising an adhesive, flexible, skin barrier product for securing the appliance to the user's skin, said skin barrier having a hole for receiving a stoma, ureter or catheter, and said skin barrier comprising, in the surface to be secured to the user's skin, at least a first zone showing adhesive and barrier properties and a second zone showing moisture absorbing properties wherein the first zone comprises a substantially homogeneous mixture of from 15 to 95% by weight of one or more rubbery components and from 2 to 85% by weight of a starch, and furthermore may comprise from 0 to 60% by weight of a one or more hydrocolloids, from 0 to 50% by weight of one or more tackifier resins, from 0 to 10% by weight of one or more plasticizers and from 0 to 5% by weight of a pigment.

It has been found that it is possible to shift the hardness of a barrier adhesive without changing significantly the curve for tan $\delta$ ($G''/G'$) by addition of starch increasing the shear modulus ($G^*$) of the adhesive to the same level as for the moisture absorbing adhesive.

It has surprisingly been found that when adding a starch in a unmodified form, i.e. non-hydrolysed form, to a skin friendly adhesive for ostomy use, the starch does not act absorbing when included in the adhesive matrix, rather as a filler.

Furthermore, the addition of starch makes the barrier adhesive, in a dry state, "behave" Theologically as an adhesive comprising hydrocolloid but which does not swell in the presence of moisture. Furthermore, it has been found that it is possible to provide a barrier layer comprising hydrocolloids and showing low absorption and being Theologically similar to conventional moisture absorbing adhesives comprising hydrocolloids by adding a starch.

Using the adhesives of the invention, a low absorption giving a greater resistance against leaching is obtained leading to a reduced degree of swelling and hence, a prolongation of the service time of an adhesive plate.

The starch may be present in the adhesive compositions of the invention in an amount from about 1% to about 90%, more preferably from 2 to 85%, shifting the rheological and absorbing properties of the barrier layer solving the above problems. The starch is preferably present in the adhesive compositions of the invention in amounts of 5–50%.

Starches being suitable for use according to the invention are purified starches from natural sources such as potato starch, corn starch, wheat starch or pea starch.

It has been found that addition of potato starch and corn starch produce the desired properties changing the rheological properties of the adhesive without imparting any noteworthy absorbing properties. Especially preferred is potato starch.

In a system of the kinds disclosed in the above patent references the moisture absorbing adhesive may suitably have the following general composition: From 15–60% of one or more rubbery components, from 20–60% of a one or more hydrocolloids, from 0–50% of one or more tackifier resins, from 0–10% of one or more plasticizer and from 0–5% of a pigment.

The barrier adhesive may suitably have the following composition: From 15–100% of a substantially homogeneous mixture of one or more rubbery components, from 0–60% of a one or more hydrocolloids, from 0–50% of one or more tackifier resins, from 0–10% of one or more plasticizers and from 0–5% of a pigment.

An adhesive barrier member (or base plate) and an outer receiving member or bag for use in an ostomy appliance according to the invention may be made from materials conventionally used for the preparation of ostomy appliances in a manner known per se in the field.

The adhesive of the invention preferably comprises a plastic or elastomeric matrix having hydrocolloid particles dispersed therein.

The elastomeric matrix may e.g. be based on polyisobutylene, butyl rubber, styrene blockcopolymers, polyacrylates or acrylate copolymers, silicone rubber, natural rubber, polyurethane rubber, polyvinylether and mixtures thereof.

One suitable elastomeric matrix may be based on polyisobutylene, butyl rubber and a hydrocolloid.

Such an adhesive typically comprises from 10 to 50% (w/w) polyisobutylene, from 5 to 30% (w/w) butyl rubber, from 0 to 15% (w/w) tackifying resin and from to 55% (w/w) of hydrocolloid.

Another suitable matrix may be based on an adhesive matrix comprising a blockcopolymer comprising styrene and one or more olefins and/or dienes, e.g. olefins or dienes having 4–6 carbon atoms, preferably having 4 carbon atoms, such as 1-butene, isoprene or butadiene. The blockcopolymer may e.g. be a styrene-isoprene copolymer or a styrene-butadiene-styrene copolymer.

Typically such an adhesive comprises from 5 to 30% (w/w) styrene-isoprene-styrene blockcopolymer, from 15 to 50% (w/w) tackifying resin and from 25 to 55% (w/w) of hydrocolloid, and from 0 to 25% (w/w) of plasticizer.

Suitable hydrocolloids for incorporation in the adhesive compositions of the invention are selected from naturally occurring hydrocolloids, semisynthetic hydrocolloids and synthetic hydrocolloids.

More particularly, the hydrocolloids may be guar gum, locust bean gum (LBG), pectin, alginates, gelatine, xanthan, gum karaya; cellulose derivatives (e.g. salts of carboxymethylcellulose such as sodium carboxymethylcellulose, methylcellulose, hydroxyethyl cellulose and hydroxypropylmethylcellulose), sodium starch glycolate, polyvinylalcohol and/or polyethylene glycol.

It is preferred to use a combination of two or more hydrocolloids. It is especially preferred to use pectin, hydroxyethyl cellulose and carboxymethylcellulose as the hydrocolloid component. A tackifying resin is preferably a hydrocarbon tackifier resin and is more preferably selected from the group comprising polymers and copolymers of cyclopentadiene, dicyclopentadiene, alpha-pinene or beta-pinene tackifier resins, conventionally used for the preparation of adhesives for ostomy appliances.

Plasticizers for use in the present invention may be conventionally used for the preparation of adhesives for ostomy appliances such as phthalates, e.g. dioctyl phthalate, or adipates, e.g. dioctyl adipate, preferably an adipate, or an oil such as liquid paraffin.

The pigment optionally being present in the compositions according to the invention may be any pharmaceutically acceptable pigment such as zinc oxide or titanium dioxide.

An adhesive skin barrier according to the invention may be a conventionally flat barrier or it may have a convex shape due to the presence of stiffening element having a convex shape.

The adhesive skin barrier of the invention is preferably provided with a border adhesive having a composition providing a transparent adhesive composition comprising hydrocolloids in which the transparency has proven to be pronounced even in adhesive plates having a considerable thickness which will facilitate checking whether a canal is being formed which may lead to a leakage.

It has been found that transparent adhesives compositions for use as border adhesives may also be composed according to the invention comprising hydroxyethyl cellulose and potato starch. Thus, it is possible, according to the invention, to provide an ostomy body side member having a central Swiss roll type helix composed of two different adhesives comprising hydrocolloids and starch in different proportions and showing barrier and absorbing properties, respectively, and even to provide such a body side member with a transparent border adhesive comprising hydrocolloids and starch, i.e. to have three different adhesives fulfilling different purposes, all comprising hydrocolloids and starch, which constitutes a preferred embodiment of the invention. In another aspect the invention relates to an adhesive flexible skin barrier product for use as a semi-manufacture in the production of dressings, skin and wound care devices, fastening means for wound care devices, fastening means for dressings, ostomy equipment, wound drains and continence equipment such as external catheters for men and for similar applications and for use in electrodes for application to the skin, said skin barrier product comprising, in the surface to be secured to the user's skin, at least a first zone showing adhesive and barrier properties and a second zone showing moisture absorbing properties wherein the first zone comprises a substantially homogeneous mixture of from 15 to 95% by weight of one or more rubbery components and from 2 to 85% by weight of a starch, and furthermore may comprise from 0 to 60% by weight of one or more hydrocolloids, from 0 to 50% by weight of one or more tackifier resins, from 0 to 10% by weight of one or more plasticizers and from 0 to 5% by weight of a pigment.

In a further aspect, the invention relates to the use of a starch for modifying of the absorbing and rheological properties of a zone of an adhesive, flexible, skin barrier product layer for an ostomy appliance, said zone comprising a substantially homogeneous mixture of from 15 to 98% by weight of one or more rubbery components and furthermore may comprise from 0 to 60% by weight of a one or more hydrocolloids, from 0 to 50% by weight of one or more tackifier resins, from 0 to 10% by weight of one or more plasticizers and from 0 to 5% by weight of a pigment.

The invention is explained more in detail in the below Examples setting forth preferred embodiments of the invention.

MATERIALS AND METHODS

Water Absorption Measurement

The adhesive was pressed into a plate with a thickness of 1 mm. A sample of 25×25 mm was then punched out and adhered on an object glass (slide). The object glass with the sample was weighed and placed in a beaker with 0,9% isotonic saline at 37° C. After 2 hours, the object glass with the sample was removed from the beaker, the water was shaken off, and the object glass with the sample was weighed again after drying the surface of the object glass not covered with adhesive. The increase of weight was recorded as the water absorption.

Dynamic Cylinder Saline Leaching of Adhesive Plates

The leaching of adhesives (in millimeters) and a qualitative evaluation of the swelling of an adhesive plate during influence of physiological saline was carried out using a roller system for rolling bottles having an inner diameter of 100 mm and an inner length of 110 mm, two frames for fixing the specimen and a fixing plate with holes for fixing the frames to the bottom of the bottle, LLDPE sheet (AS400 Item number 12796135, 12796180 or 12796270)

Cutting punches 55/25 mm and 70/48 mm

Cutting punch 10 cm×10 cm 0,9% physiological saline

Water resistant tape for sealing the outer edge of the specimen, and Silicone grease.

Procedure

Preparation of Specimen:

The adhesive to be tested was pressed between two pieces of silicone paper for producing an adhesive plate having a thickness of 1 mm and then laminated with LLDPE sheet. An adhesive ring having a diameter of 55 mm and an opening of 25 mm was punched out. Then, an adhesive ring of water resistant tape (mask) having a diameter of 70 mm and a hole of 48 mm was punched out, and the mask was placed and centred on the surface of the adhesive ring with the backing layer.

For mounting the specimen, a piece of PE sheet of the size 10×10 cm was punched out, silicone paper was removed from the back of the specimen and the specimen was adhered to the PE sheet avoiding entrapment of air bubbles.

The mounted adhesive plate was left for conditioning at 23° C. for 18 hours and then placed between two frames, one of which was provided with a rubber gasket for fixing and stretching the sheet.

The assembled frame was fixed to the cover of the bottle and to the fixing plate with holes and the bottle was filled with 400 ml 0.9% physiological saline.

The cover was placed on the bottle after greasing of the o ring of the cover with silicone grease, and the bottle was placed on the roller system and rolled for 112 hours.

After opening the bottle, the specimen was inspected and the leached zone of the adhesive of the specimen from the centre was measured in mm (treble determination).

PIB: Polyisobutylene available under the trademark Vistanex from Exxon Chemical Co. as grade LM-MH Butyl rubber: Polysar butyl 101-3 from Bayer AG Kraton D1107 CU: Styrene-isoprene-styrene copolymer having a molecular weight of 212,000–260,000 (GPC) from Shell Chemicals Arkon P90: A saturated Alicyclic hydrocarbon resin of petrochemical origin from Arakawa Forest Chemical industries Ltd. Molecular weight is 630 g/mole.

Arkon P115: A saturated Alicyclic hydrocarbon resin of petrochemical origin from Arakawa Forest Chemical industries Ltd. Molecular weight is 770 g/mole.

Regalite R91: A saturated hydrocarbon resin of petrochemical origin from Hercules. Molecular weight is 700 g/mole.

DOA oil: Dioctyl adipate, commercially available from several suppliers, i.a BP Chemicals Natrosol 250 HX Pharm from Aqualon, a division of Hercules Inc. It is a water soluble hydroxy ethyl cellulose (cellulose etherified with ethylene oxide) with low particle size, 95% is below 250 microns.

CMC: Sodium carboxymethylcellulose available under the trademark Blanose 9H4XF from Aqualon/Hercules Pectin: GENU PEKTIN POMOSIN LM 12 CG-Z/200 from Hercules Copenhagen A/S Potato starch:

Kartoffelmel produced by Cerestar for Dansk Supermarked, DVN 1006:4,

C Gel 30002 from Cerestar, or

4 available from KMC.

A Z mixer Type LKB 025 from Herman-Linden was used.

Experimental Part

Reference Example A

A Swiss Roll adhesive system of the type disclosed in WO 89/05619 comprising two adhesives having the compositions shown in the below table 1 was produced.

The moisture absorbing adhesive was produced from a pre-mixture comprising 26.90% PIB, 43.90% butyl rubber and 29.2% Arkon P115 by mixing at 120° C. for minutes in a Z mixer.

68.4 grams of pre-mixture was added to a Z mixer and heated to 95° C. under mixing. Then, 41.60 grams of PIB was added and the mixing continued for 10 minutes. 70 grams of pectin and 20 grams of CMC were added and mixed for 20 minutes at 95° C. and under a vacuum of 100 mbar until a homogeneous dough-like mass was formed.

The resulting brown and tough mass was then removed from the mixer while hot and soft and formed into approximately 1 mm thick sheet stock material by compression moulding the adhesive mass at approximately 90° C. and 100 Bars between two sheets of silicone paper. The resultant flat plate was cut into the desired pieces for testing.

The barrier adhesive was produced from a premixture comprising 68.18% PIB, and 31.82% butyl rubber by mixing at 95° C. for 15 minutes in a Z mixer.

58.70 grams of pre-mixture was added to a Z mixer and heated to 95° C. under mixing. Then, 141.30 grams of PIB was added and the mixing continued for 10 minutes. The resulting transparent chewing-gum-like mass was formed into approximately 1 mm thick sheet stock material by compression moulding the adhesive mass at approximately 90° C. and 100 Bars between two sheets of silicone paper. The resultant flat plate was cut into the desired pieces for testing.

TABLE 1

| Constituent | Moisture absorbing part of roll (Δ) | Barrier part of roll (X) |
|---|---|---|
| PIB | 30.00 | 80.00 |
| Butyl rubber | 15.00 | 20.00 |
| Arkon P90 | | |
| Arkon P115 | 10.00 | |
| CMC | 10.00 | |
| Pectin | 35.00 | |

EXAMPLES 1–2

In an analogous manner as disclosed in Example A Swiss Roll adhesive systems of the type disclosed in WO 89/05619 comprising two adhesives barriers according to the invention were produced. The moisture absorbing part of the roll had the composition stated in Example A Compositions of the barrier part of an adhesive skin barrier according to the invention are shown in the below Table 2.

TABLE 2

| Component | Barrier part of roll Example 1 (□) | Barrier part of roll Example 2 (○) |
|---|---|---|
| PIB | 48.00 | 30.00 |
| Butyl rubber | 12.00 | 15.00 |
| Regalite R91 | | 10.00 |
| Potato starch | 40.00 | 45.00 |

By changing the composition of the barrier part of the roll it was possible to solve the problem with itching presumably being caused by the great difference in the rheological properties of the moisture absorbing part of the roll and the barrier part of the roll. This was confirmed in a test using voluntary healthy persons.

The barrier adhesive of Example 1 is based on the polymeric blend of the barrier part of the adhesive roll of Example A, and the barrier adhesive of Example 2 is based on the polymeric blend of the moisture absorbing part of the adhesive roll of Example A

EXAMPLE 3

Test of rheological properties.

A rheometer from Haake: RheoStress RS 150 was used. It was thermostated using a Haake DC10 thermostat and a water bath Haake K20, Sensor 8 mm plate/plate geometry.

A frequency sweep (CD (Controlled Deformation) 1%, 32° C.) was carried out testing specimen in the form of wafers of a thickness of 1 mm and a diameter of 8 mm of the adhesive compositions of Examples A, 1 and 2.

Frequency spectrum 0.001–100.000 Hz (G*) and 0.01–100.000 Hz (tan δ)

Total viscoelastic modulus (G*) and tan δ were determined.

The latter is the proportion between the viscous modulus (designated G") and the elastic modulus (designated G'). To put it shortly, the greater the tan δ, the more viscous properties and tendency of the product to flow under a given stress as opposed to the more elastic properties of materials having a low tan δ.

The results are shown in the drawings showing a graphical representation of (G*) and tan δ as a function of the frequency. The adhesives are marked as indicated above and G* (Upper curves increasing with the frequency) is plotted against the first y-axis and the tan δ plotted against the second y-axis.

It appears that the rheological properties of adhesives modified with potato starch are more similar to the rheological properties of the moisture absorbing adhesive than the unmodified barrier adhesive composition.

EXAMPLES 4–5

Production of adhesives according to the invention showing low water absorption and being suitable for use as border of an ostomy appliance and having the compositions stated in Table 3.

A premixture producing adhesives of the invention was produced by mixing a mixture comprising 68,18% butyl rubber and 31,82% Vistanex LM at 95° C. for 1 hour in a Z-blade mixer.

Preparation of composition of Example 4:

58.7 grams of this premixture was added to a Z-blade mixer and heated to 95° C. during mixing. Then, further 11.3 grams of Vistanex LM and 30 grams of Arkon P-90 was added and the mixing was continued for 30 minutes. Finally, 40 grams of Natrosol 250 HX Pharm and 60 grams of potato starch were added and mixed under a vacuum of 100 mbar for 1 hour until a homogeneous dough-like mass was formed.

The white mass was removed from the mixer while hot and soft and formed into approximately 1 mm thick sheet stock material by compression moulding the adhesive mass at approximately 90° C. and 100 bars between two sheets of siliconized paper. The resulting flat plate was cut into the pieces of the desired sizes for testing.

The adhesive composition of Example 5 was prepared in an analogous manner as disclosed in Example 4 using 30 grams of Natrosol 250 HX Pharm and 70 grams of potato starch.

TABLE 3

Adhesives according to the invention being suitable as border of an ostomy appliance

| Constituent | Example 4 | Example 5 |
|---|---|---|
| Butyl rubber 101-3 | 20.00 | 20.00 |
| Vistanex LM | 15.00 | 15.00 |
| Arkon P90 | 15.00 | 15.00 |
| Natrosol 250 HX Pharm | 20.00 | 15.00 |
| Potato starch, C gel 30002 | 30.00 | 35.00 |
| Total percent | 100.00 | 100.00 |

REFERENCE EXAMPLE B

In an analogous manner as disclosed in Example 4 but using 100 grams of Natrosol 250 HX Pharm and no potato starch a reference adhesive for the border of an ostomy appliance was produced having the composition stated in Table 4

TABLE 4

| Constituent | Reference Example B |
|---|---|
| Butyl rubber 101-3 | 20.00 |
| Vistanex LM | 15.00 |
| Arkon P90 | 15.00 |

TABLE 4-continued

| Constituent | Reference Example B |
|---|---|
| Natrosol 250 HX Pharm | 50.00 |
| Potato starch C gel 30002 | 0.00 |
| Total percent | 100.00 |

The use of hydroxy ethyl cellulose in the border adhesive has been proven to provide transparent adhesive compositions comprising hydrocolloids in which the transparency is pronounced even in adhesive plates having a considerable thickness.

EXAMPLE 6

Comparison of water absorption of adhesive compositions of Examples 4–5 with adhesive composition of Reference Example B.

The water absorption of the adhesive compositions of Examples 4–5 and Reference Example B was compared as disclosed above. The results are presented in the below Table 5:

TABLE 5

| Water absorption | Reference Example B | Example 4 | Example 5 |
|---|---|---|---|
| Water absorption after 2 hours at 37° C. (g/cm²) | 0.27 | 0.14 | 0.11 |

As appears from Table 5, the water absorption is lowered considerably by substituting hydroxy ethyl cellulose with potato starch. The absorption is reduced by about 50% by reducing the contents of hydroxy ethyl cellulose from 50% to 20%. Thus it appears that potato starch does not act absorbing when included in the adhesive matrix, rather as a filler. The composition of Example 4 has proven very suitable for use as border adhesive.

EXAMPLES 7–8

Preparation of adhesive compositions according to the invention showing low absorption and suitable for use as a barrier layer and having the compositions stated in Table 6 and determination of the water absorption.

A premixture producing adhesives of the invention was produced by mixing 37.9% Kraton D-1107CU 52.4% and 31.82% Arkon P90 and 7.9% DOA oil at 1 60° C. for 30 minutes in a Z-blade mixer.

Preparation of composition of Example 8:
126.8 grams of the premixture was added to a Z-blade mixer and heated to 90° C. under mixing. To this mixture, 40 grams of Blanose 9H4XF and 33.2 grams of potato starch (C gel 30002 from Cerestar) were added and mixed under a vacuum of 100 mbar for 1 hour until a homogeneous dough-like mass was formed.

The resulting white and tough mass was removed from the mixer while hot and soft and formed into approximately 1 mm thick sheet stock material by compression moulding the adhesive mass at approximately 90° C. and 100 bars between two sheets of siliconized paper. The resultant flat plate was cut into the pieces of the desired sizes for testing.

The adhesive composition of Example 7 was prepared in an analogous manner as disclosed in Example 8 using 60 grams of Blanose 9H4XF and 13.2 grams of potato starch.

The water absorption of the adhesive compositions of Examples 7–8 was determined as disclosed above with the proviso that absorption was determined after 18 hours instead of after 2 hours due to the low absorption. The results demonstrating that substitution of CMC by potato starch reduces the water absorption are also presented in the below Table 6.

TABLE 6

| Constituent | Example 7 | Example 8 |
|---|---|---|
| Kraton D-1107CU | 24.00 | 24.00 |
| Arkon P90 | 34.40 | 34.40 |
| DOA oil | 5.00 | 5.00 |
| CMC, Blanose 9H4XF | 30.00 | 20.00 |
| Kartoffelmel, C Gel 30002 | 6.60 | 16.60 |
| Total percent | 100.00 | 100.00 |
| Water absorption after 18 hours at 37° C. (g/cm²) | 0.26 | 0.04 |

EXAMPLES 9–11

Preparation of adhesive compositions according to the invention showing water absorption and low swell and having the compositions stated in Table 7 and determination of the water absorption.

Preparation of composition of Example 10:126.8 grams of the premixture produced in Example 7 was added to a Z-blade mixer and heated to 90° C. during mixing. To this mixture, 10 grams of potato starch, 40 grams of GENU Pectin and 23.2 grams of Natrosol were added and mixed under a vacuum of 100 mbar for 1 hour until a homogeneous dough-like mass was formed.

The resulting white and tough mass was removed from the mixer while hot and soft and formed into approximately 1 mm thick sheet stock material by compression moulding the adhesive mass at approximately 90° C. and 100 bars between two sheets of siliconized paper. The resultant flat plate was cut into the pieces of the desired sizes for testing.

The adhesive compositions of Example 9 and 11 were prepared in an analogous manner as disclosed in Example 10 using 33.2 grams of Natrosol 250 HX Pharm and no potato starch and 13.2 grams of Natrosol 250 HX Pharm and 20 grams of potato starch, respectively.

The water absorption of the adhesive compositions of Examples 9–11 was determined as disclosed above with the proviso that absorption was determined after 18 hours instead of after 2 hours due to the low absorption. The results are also presented in the below Table 7

TABLE 7

| Constituent | Example 9 | Example 10 | Example 11 |
|---|---|---|---|
| Kraton D-1107CU | 24.00 | 24.00 | 24.00 |
| Arkon P90 | 34.40 | 34.40 | 34.40 |
| DOA oil | 5.00 | 5.00 | 5.00 |
| Potato starch, #4 KMC | | 5.00 | 10.00 |
| GENU Pectin | 20.00 | 20.00 | 20.00 |
| Natrosol 250 HX Pharm | 16.60 | 11.60 | 6.60 |
| Total percent | 100.00 | 100.00 | 100.00 |
| Water absorption after 18 hours at 37° C. (g/cm²) | 0.18 | 0.14 | 0.07 |

The results demonstrate that potato starch acts as a filler not absorbing when included in the adhesive matrix.

EXAMPLE 12

Test of ostomy appliances having an adhesive plate according to the invention as compared to a commercially available ostomy appliance.

The adhesive compositions prepared in Examples 8 and 10 were formed into a Swiss roll adhesive base plate of the type disclosed in WO 89/05619.

A commercially available product available under the trademark Assura collection with adhesive for long wear-time (with zinc oxide) was used for comparison.

The test was carried out by Dynamic Cylinder Saline Leaching of Adhesive Plates.

The results after 112 hours showed that the adhesive plate according to the invention only showed a few mm leaching of the edge whereas the commercial product showed about 20 mm leaching.

Thus, the adhesive according to the invention showed stronger erosion resistance, and thus, improved service time as compared to the Assura appliance with adhesive for long wear-time (with zinc oxide).

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. An ostomy appliance comprising an adhesive, flexible, skin barrier product for securing the appliance to a user's skin, said skin barrier product having a hole for receiving a stoma, ureter or catheter, and including, in an adhesive surface to be secured to the user's skin, at least a first zone showing adhesive and barrier properties and a second zone showing moisture absorbing properties, said first zone including a substantially homogeneous mixture of from 15 to 95% by weight of one or more rubbery components and from 2 to 85% by weight of a starch for modifying absorbency and rheological properties of said first zone.

2. The ostomy appliance as claimed in claim 1 further comprising a border constituted of an adhesive consisting essentially of butyl rubber, PIB, a saturated hydrocarbon resin, hydroxyethyl cellulose, and potato starch.

3. The adhesive, flexible, skin barrier product of claim 1, wherein said first zone further includes 10–50% by weight polyisobutylene, 5–30% by weight butyl rubber, and 25–55% by weight of one or more hydrocolloids.

4. The adhesive, flexible, skin barrier product of claim 1, wherein said first zone further includes 5–30% by weight styrene-isoprene-styrene blockcopolymer, 25–55% by weight of one or more hydrocolloids and 15–50% by weight of one or more tackifier resins.

5. The adhesive, flexible, skin barrier product of claim 1, wherein the starch is present in an amount from 5–50%.

6. An adhesive flexible skin barrier product for use as a semi-manufacture in the production of dressings, skin and wound care devices, fastening means for wound care devices, fastening means for dressings, ostomy equipment, wound drains and incontinence equipment such as external catheters and for similar applications and for use in electrodes for application to the skin, said skin barrier product comprising, in an adhesive surface to be secured to the user's skin, at least a first zone showing adhesive and barrier properties and a second zone showing moisture absorbing properties, said first zone including a substantially homogeneous mixture of from 15 to 95% by weight of one or more rubbery components and from 2 to 85% by weight of a starch.

7. The adhesive, flexible, skin barrier product of claim 6, wherein said first zone further includes 10–50% by weight polyisobutylene, 5–30% by weight butyl rubber, and 25–55% by weight of one or more hydrocolloids.

8. The adhesive, flexible, skin barrier product of claim 6, wherein said first zone further includes 5–30% by weight styrene-isoprene-styrene blockcopolymer, 25–55% by weight of one or more hydrocolloids and 15–50% by weight of one or more tackifier resins.

9. The adhesive, flexible, skin barrier product of claim 6, wherein the starch is present in an amount from 5–50%.

* * * * *